US010908082B2

(12) United States Patent
Kobayashi et al.

(10) Patent No.: US 10,908,082 B2
(45) Date of Patent: Feb. 2, 2021

(54) GAS ANALYZER

(71) Applicant: Yokogawa Electric Corporation, Tokyo (JP)

(72) Inventors: Yoshitaka Kobayashi, Musashino (JP); Junichi Matsuo, Musashino (JP); Naoyuki Fujimura, Musashino (JP)

(73) Assignee: YOKOGAWA ELECTRIC CORPORATION, Tokyo (JP)

( * ) Notice: Subject to any disclaimer, the term of this patent is extended or adjusted under 35 U.S.C. 154(b) by 0 days.

(21) Appl. No.: 16/376,765

(22) Filed: Apr. 5, 2019

(65) Prior Publication Data

US 2019/0317018 A1    Oct. 17, 2019

(30) Foreign Application Priority Data

Apr. 16, 2018    (JP) .................................. 2018-078474

(51) Int. Cl.
*G01N 21/39* (2006.01)
*G02B 27/14* (2006.01)
(Continued)

(52) U.S. Cl.
CPC ............... *G01N 21/39* (2013.01); *G01J 3/42* (2013.01); *G02B 27/14* (2013.01); *H01S 5/0071* (2013.01);
(Continued)

(58) Field of Classification Search
CPC ............................ G01J 2003/423; G01J 3/42; G01N2 021/399; G01N 2021/8521; G01N 2021/8578; G01N 21/3504; G01N 21/39; G01N 21/8507; G01N 33/0009; G02B 27/14; H01S 5/0071
See application file for complete search history.

(56) References Cited

U.S. PATENT DOCUMENTS

| 8,928,885 B1 | 1/2015 | Luo et al. |
| 2012/0113426 A1 | 5/2012 | Rao |

(Continued)

FOREIGN PATENT DOCUMENTS

| CN | 104215606 A | 12/2014 |
| EP | 1508794 A1 | 2/2005 |

(Continued)

*Primary Examiner* — Hina F Ayub
*Assistant Examiner* — Amanda H Merlino
(74) *Attorney, Agent, or Firm* — Osha Bergman Watanabe & Burton LLP (57) ABSTRACT

A gas analyzer includes an optical emitter that irradiates measurement light into a measurement region including a measured-gas, a first optical receiver that receives the measurement light passing through the measurement region, a splitting unit between the optical emitter and the measurement region that splits off a portion of the measurement light irradiated from the optical emitter to yield reference light, a reference unit, and an optical component. The reference unit holds a gas containing a measurement target component identical with the measured-gas but at a known concentration and a second optical receiver that receives the reference light passing through the region including the gas. The optical component is disposed between the splitting unit and the region and expands the beam diameter of the reference light to be larger at the second optical receiver than the receiving diameter of the second optical receiver.

6 Claims, 6 Drawing Sheets

(51) Int. Cl.
 *G01J 3/42* (2006.01)
 *H01S 5/00* (2006.01)
(52) U.S. Cl.
 CPC .. *G01J 2003/423* (2013.01); *G01N 2021/399* (2013.01)

(56) References Cited

U.S. PATENT DOCUMENTS

| | | |
|---|---|---|
| 2015/0041660 A1 | 2/2015 | Trollsch |
| 2015/0276587 A1 | 10/2015 | Cowie et al. |
| 2017/0205336 A1 | 7/2017 | Ido |

FOREIGN PATENT DOCUMENTS

| | | |
|---|---|---|
| JP | 2009115711 A | 5/2009 |
| JP | 2010-185694 A | 8/2010 |
| JP | 2017129374 A | 7/2017 |
| JP | 2017142346 A | 8/2017 |

GAS ANALYZER

CROSS-REFERENCE TO RELATED APPLICATION

The present application claims priority to and the benefit of Japanese Patent Application No. 2018-078474 filed Apr. 16, 2018, the entire contents of which are incorporated herein by reference.

TECHNICAL FIELD

The present disclosure relates to a gas analyzer.

BACKGROUND

An apparatus for optically calculating the concentration of a measured-gas flowing through a predetermined flow path is known, such as the gas concentration measurement apparatus disclosed in patent literature (PTL) 1.

CITATION LIST

Patent Literature

PTL 1: JPC2010185694A

SUMMARY

A gas analyzer according to an one or more embodiments includes an optical emitter configured to irradiate measurement light into a measurement region including a measured-gas; a first optical receiver configured to receive the measurement light after the measurement light passes through the measurement region; a splitting unit disposed between the optical emitter and the measurement region and configured to split off a portion of the measurement light irradiated from the optical emitter to yield reference light; a reference unit comprising a gas, identical to a measurement target component in the measured-gas, at a known concentration and a second optical receiver configured to receive the reference light after the reference light passes through a region of the reference unit including the gas; and an optical component disposed between the splitting unit and the region including the gas. The optical component is configured to expand a beam diameter of the reference light to be larger at the second optical receiver than a receiving diameter of the second optical receiver.

DETAILED DESCRIPTION

Specific embodiments of the invention will be described in detail with reference to the accompanying figures. In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description. The gas concentration measurement apparatus according to one or more embodiments may further include a reference unit to allow detection of the wavelength position of the absorption spectrum peak of a measurement target component. Additionally, a gas analyzer 1 may further include an alignment mechanism for correcting the beam position of an optical emitter 21 in accordance with attachment requirements or attachment circumstances such as disturbance. If the beam position of the optical emitter 21 is changed from the standard position by such an alignment mechanism, the amount of light received by the optical receiver of the reference unit also changes.

In one or more embodiments of the present invention disclosed herein, a gas analyzer may be provided in which the amount of reference light received by the optical receiver of the reference unit is stable, even when the beam position of the optical emitter changes from the standard position.

A gas analyzer according to one or more embodiments includes an optical emitter configured to irradiate measurement light into a measurement region including a measured-gas; a first optical receiver configured to receive the measurement light after the measurement light passes through the measurement region; a splitting unit (beam splitter) disposed between the optical emitter and the measurement region and configured to split off a portion of the measurement light irradiated from the optical emitter to yield reference light; a reference unit that holds a gas, identical to a measurement target component in the measured-gas, at a known concentration and a second optical receiver configured to receive the reference light after the reference light passes through a region of the reference unit including the gas; and an optical component disposed between the splitting unit and the region including the gas. The optical component is configured to expand a beam diameter of the reference light to be larger at the second optical receiver than a receiving diameter of the second optical receiver. The amount of the reference light received at the second optical receiver is stable in this configuration, even when the beam position of the optical emitter changes from the standard position. Accordingly, it is easy to detect the wavelength position of the absorption spectrum peak of the gas, which is identical to the measurement target component, filling the reference unit. In this way, measurement with the gas analyzer that uses the reference unit has better resistance to changes in the beam position of the optical emitter.

In the gas analyzer according to one or more embodiments, the optical component may include an optical lens configured to condense the reference light.

In the gas analyzer according to one or more embodiments, the optical lens may be configured to make a focal point of the reference light in the reference unit closer to the optical lens. The optical lens can thereby further increase the beam diameter of the reference light on the second optical receiver.

In the gas analyzer according to one or more embodiments, the optical lens may be a plano-convex lens, and the flat surface of the plano-convex lens may face the reference unit.

The gas analyzer according to one or more embodiments may further include a first reflector disposed between the splitting unit and the optical component and configured to reflect the reference light split off by the splitting unit towards the optical emitter. The analysis unit overall, including the optical emitter, the first optical receiver, the splitting unit, the second optical receiver, the reference unit, the optical component, and the first reflector, thus becomes more compact. Specifically, the interior space of the analysis unit is efficiently used even when electronic components and optical components are arranged together inside the analysis unit, since the optical path of the reference light turns back because of the first reflector.

The gas analyzer according to one or more embodiments may further include a probe extending along an optical axis of the measurement light so as to overlap the measurement region and a second reflector positioned at an opposite tip of the probe from the optical emitter and configured to reflect the measurement light after the measurement light passes through the measurement region. The first optical receiver may be configured to receive the measurement light reflected by the second reflector. The gas analyzer can, for example, thereby be configured as a probe-type gas analyzer in which a light source, a reflecting structure, and a photodetector are integrally built into the gas analyzer.

The present disclosure can provide a gas analyzer in which the amount of reference light received by the optical receiver of the reference unit is stable, even when the beam position of the optical emitter changes from the standard position.

Embodiments of the present disclosure are described below with reference to the drawings. The front-back, left-right, and up-down directions referred to below are based on the directions of the arrows in the drawings. The directions of the arrows are consistent in FIG. 1 through FIG. 6.

An example in which a measured-gas G flows upward from below in each drawing is described below. The flow direction of the measured-gas G is not limited to this case. The measured-gas G may flow in any direction, and a gas analyzer 1 according to one or more embodiments may be arranged in any direction in accordance with the flow direction of the measured-gas G.

Figure 1:
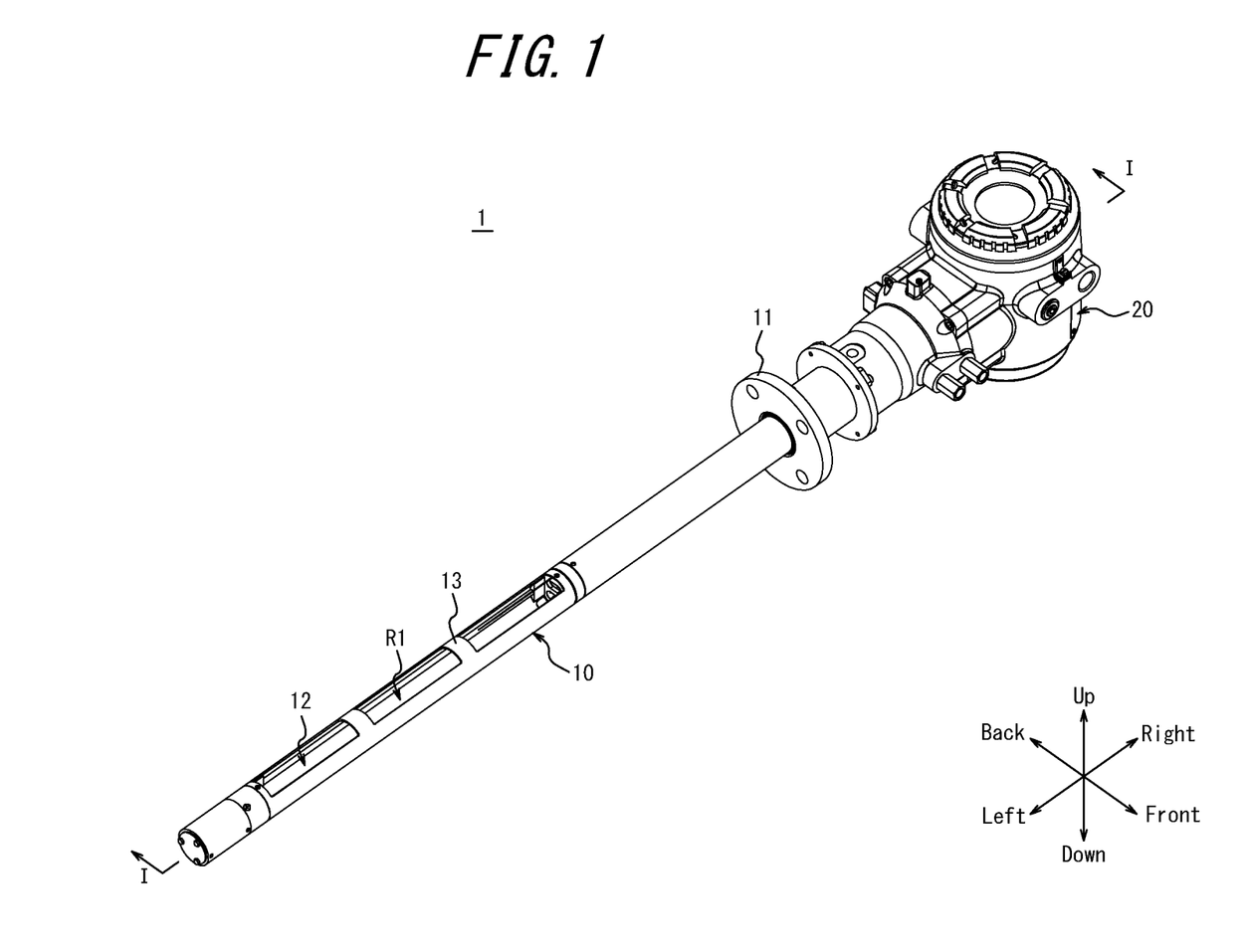
FIG. 1 is a perspective view from above illustrating a gas analyzer according to one or more embodiments.
Figure 2:
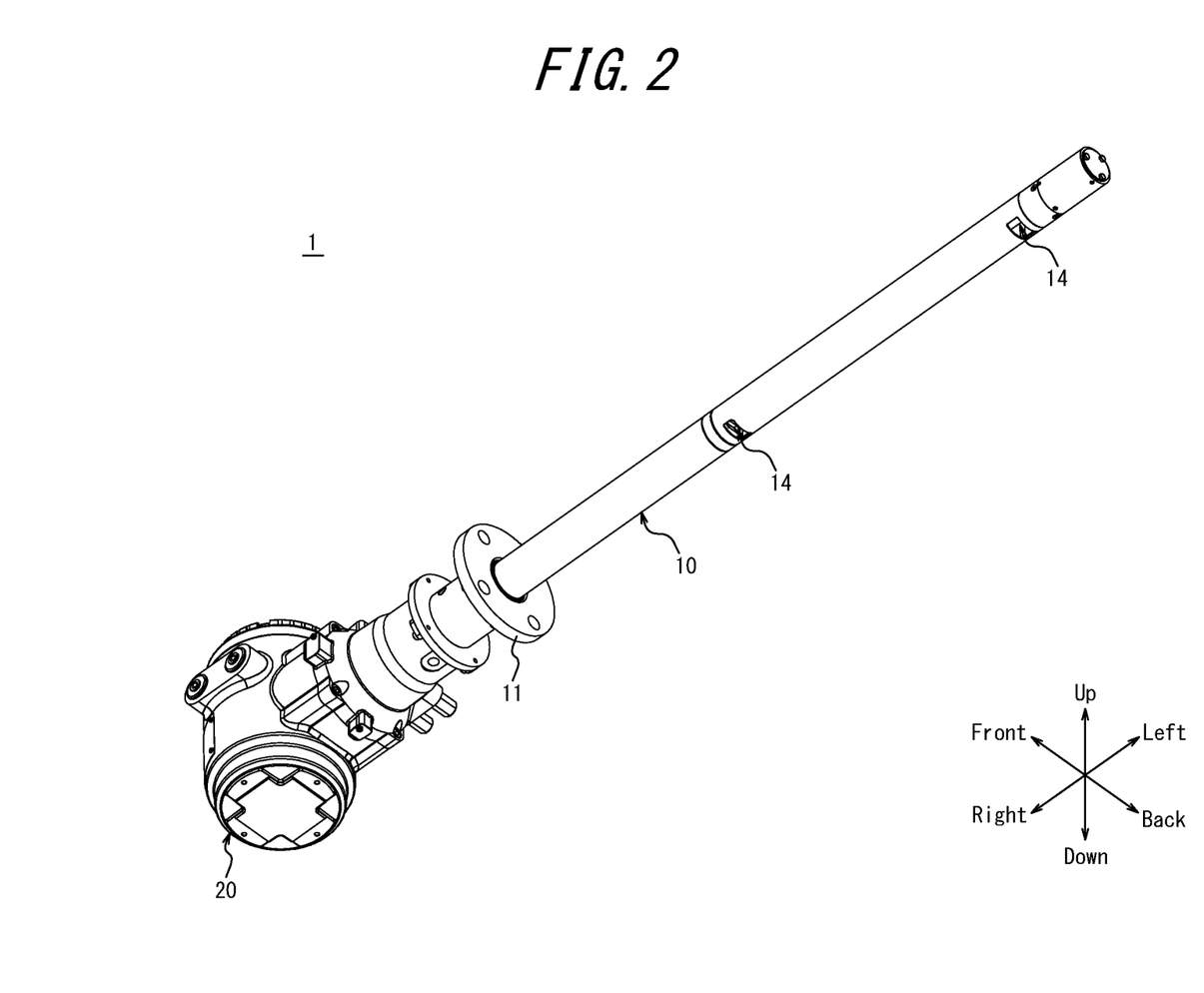
FIG. 2 is a perspective view from below illustrating the gas analyzer of FIG. 1.
Figure 3:
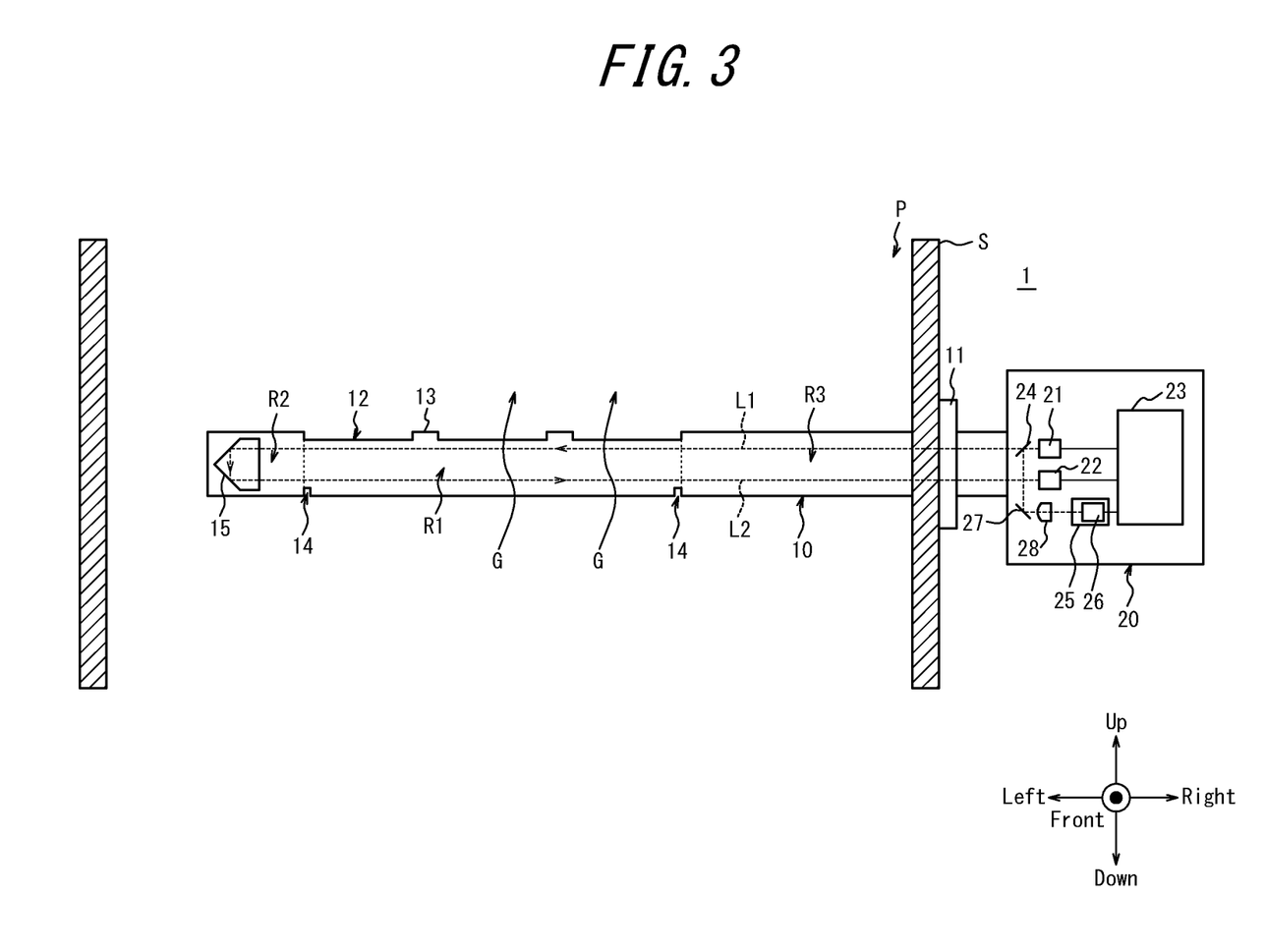
FIG. 3 is a schematic cross-section along the I-I arrows in FIG. 1.

FIG. 1 is a perspective view from above illustrating the gas analyzer 1 according to one or more embodiments. FIG. 2 is a perspective view from below illustrating the gas analyzer 1 of FIG. 1. FIG. 3 is a schematic cross-section along the I-I arrows in FIG. 1. As an example, FIG. 3 illustrates the gas analyzer 1 of FIG. 1 attached to a flue wall S to analyze the component concentration of a certain component included in the measured-gas G that flows in a flue P. For the sake of explanation, the configuration of the gas analyzer 1 according to one or more embodiments is simplified in FIG. 3. Specifically, details of the internal configuration of an analysis unit 20, such as an optical lens 21a and a condensing lens 25a, described below, are omitted in FIG. 3.

The functions and configuration of the gas analyzer 1 according to one or more embodiments are mainly described with reference to FIGS. 1 to 3.

The gas analyzer 1 is, for example, attached directly to the flow path through which the measured-gas G flows. The gas analyzer 1 analyzes the component concentration of a measurement target component. The measured-gas G may, for example, include a gas such as CO, $CO_2$, $H_2O$, $C_nH_m$ (a hydrocarbon), $NH_3$, or $O_2$. The flow path includes piping, a flue, a combustion furnace, and the like.

The gas analyzer 1 includes a probe-type tunable diode laser absorption spectroscopy (TDLAS) gas analyzer, for example, that has an explosion-proof structure and is used in an explosion-proof area. Probe-type refers, for example, to how the gas analyzer 1 has a light source, a reflecting structure, and a photodetector integrally built therein and is structured for insertion from one end into the flow path through which the measured-gas G flows. The gas analyzer 1 analyzes the component concentration of the measurement target component by irradiating a laser beam that becomes measurement light onto the measured-gas G, which includes a process gas or the like, for example.

The gas molecules included in the measured-gas G exhibit a light absorption spectrum based on the vibration and rotational energy transition of the molecules in a region from infrared to near infrared. The absorption spectrum is unique to the component molecules. By the Lambert-Beer law, the absorbance of gas molecules with regard to the measurement light is proportional to their component concentration and the optical path length. Accordingly, the component concentration of the measurement target component can be analyzed by measuring the absorption spectrum intensity.

In TDLAS, a semiconductor laser beam with a sufficiently narrower line width than the absorption line width of the energy transition of the gas molecules is irradiated onto the measured-gas G as measurement light. The wavelength of measurement light is swept by high-speed modulation of the drive current for the semiconductor laser. The optical intensity of the measurement light that passes through the measured-gas G is measured to acquire one independent absorption spectrum.

The sweep range of the laser beam differs depending on use. When the measurement target component is $O_2$, the line width of the laser light is, for example, 0.0002 nm, and the sweep width is, for example, 0.1 nm to 0.2 nm. The absorption spectrum is measured by sweeping over a sweep width of 0.1 nm to 0.2 nm. The component concentration of the measurement target component is calculated by performing concentration conversion on the acquired single absorption spectrum. Methods of concentration conversion include known methods, such as the peak height method, the spectral area method, and the 2f method.

The major components of the gas analyzer 1 are a probe 10 and an analysis unit 20. As illustrated in the example gas analyzer 1 of FIG. 3, the majority of the probe 10 extends inside the flue P, and the analysis unit 20 is supported while disposed on the outside of the flue P. Specifically, the gas analyzer 1 is supported by the flue wall S when a flange 11, formed on a portion of the probe 10, is attached to the flue wall S from the outside.

As illustrated in FIG. 1 and FIG. 2, the probe 10 is a cylindrical body with a substantially circular cross-sectional shape, for example. The external length from the outer surface of the flange 11 to the tip of the probe 10 is, for example, approximately 0.5 m to 2 m. The probe 10 is formed by any metal member. As illustrated in FIG. 3, the probe 10 extends in a substantially orthogonal direction to the flow direction of the measured-gas G inside the flue P, for example.

The probe 10 extends in the left-right direction and includes an opening 12 that opens upward, as illustrated in FIG. 1. The opening 12 exposes the corresponding interior section of the probe 10 inside the flue P. The probe 10 includes a plurality of ribs 13 provided in the opening 12 to maintain the strength of the probe 10. As illustrated in FIG. 2, the probe 10 includes notches 14 formed by cutting out a portion of the surface of the probe 10 from below, towards the inside. The notches 14 are respectively formed at substantially the same left-right positions as the left-right ends of the opening 12. The notches 14 connect the inner section of the probe 10 exposed in the flue P by the opening 12 with the space in the flue P below the inner section.

As illustrated in FIG. 3, the probe 10 includes a reflector 15 in the inner section at the tip inside the flue P. The reflector 15 includes any reflecting structure for reflecting the measurement light, such as a corner cube prism or a retroreflector.

The analysis unit 20 is attached at the opposite end from the tip of the probe 10 where the reflector 15 is attached. The analysis unit 20 is located outside of the flue P. The analysis unit 20 includes the optical emitter 21 for irradiating the measurement light onto the measured-gas G and a first optical receiver 22 for receiving the measurement light reflected by the reflector 15. The analysis unit 20 further includes a calculation unit 23. The optical emitter 21, the first optical receiver 22, and the calculation unit 23 are electrically connected via a plurality of electronic substrates. The housing of the analysis unit 20 is, for example, an explosion-proof container that stores each of these components. The analysis unit 20 has a module structure for integrally storing these components. The optical emitter 21 and the first optical receiver 22 are arranged near each other inside the analysis unit 20.

The optical emitter 21 includes any light source capable of measurement by TDLAS with respect to the measured-gas G. For example, the optical emitter 21 includes a semiconductor laser. The first optical receiver 22 includes any photodetector capable of measurement by TDLAS with respect to the measured-gas G. For example, the first optical receiver 22 includes a photodiode. The calculation unit 23 includes one or more processors. The calculation unit 23 controls overall operations of the gas analyzer 1, including the optical emitter 21 and the first optical receiver 22.

A portion of the measured-gas G flowing upward from below in the flue P flows into a measurement region R1 inside the probe 10 from below through the notches 14. Another portion of the measured-gas G wraps around and flows into the measurement region R1 inside the probe 10 through the opening 12 from above. In this way, the measured-gas G flowing through the flue P flows inside the probe 10. The measured-gas G flowing inside the probe 10 flows out into the flue P once again through the opening 12, for example. Here, the measurement region R1 includes an interior space of the probe 10 exposed to the flue P by the opening 12. In this way, the measurement region R1 is filled with the measured-gas G.

On the other hand, a purge gas is supplied by any appropriate mechanism to regions R2 and R3 formed on the left and right sides of the measurement region R1 inside the probe 10. In FIG. 3, the boundary between the measurement region R1 and the region R2 and the boundary between the measurement region R1 and the region R3 are indicated by dotted lines. The purge gas suppresses contact between the measured-gas G and optical components such as the reflector 15, the optical emitter 21, and the first optical receiver 22 to prevent problems, such as contamination or corrosion, of these optical components. The regions R2 and R3 are thus filled with the purge gas.

The notches 14 suppress mixing of the measured-gas G and the purge gas between the measurement region R1 and the regions R2 and R3. Specifically, the notches 14 guide the measured-gas G from the flue P into the measurement region R1 in the probe 10, thereby suppressing mixing of the purge gas into the measurement region R1. Similarly, the notches 14 suppress mixing of the measured-gas G into the regions R2 and R3.

The optical emitter 21 irradiates measurement light towards the reflector 15 of the probe 10. In FIG. 3, the measurement light before being reflected by the reflector 15 is indicated as emitted light L1. The optical emitter 21 irradiates the emitted light L1 into the measurement region R1 that includes the measured-gas G. The emitted light L1 propagates inside the probe 10, which extends along the optical axis of the emitted light L1 so as to overlap the measurement region R1. The emitted light L1 is then incident on the reflector 15. The reflector 15 is positioned at the opposite tip of the probe 10 from the optical emitter 21 and reflects a portion of the emitted light L1 that passed through the measurement region R1. In FIG. 3, the measurement light after being reflected by the reflector 15 is indicated as reflected light L2. The reflected light L2 again passes through the inside of the probe 10 that includes the measurement region R1. The first optical receiver 22 receives the reflected light L2 that was reflected by the reflector 15 and passed through the measurement region R1. In this manner, the measurement region R1 is arranged between the optical emitter 21 and the first optical receiver 22 in the optical path of the emitted light L1 and the reflected light L2.

The first optical receiver 22 electrically amplifies a measurement signal related to the detected measurement light using any appropriate amplifier circuit and outputs the detected optical intensity of the measurement light to the calculation unit 23 as a scan signal. A portion of each of the emitted light L1 and the reflected light L2 is absorbed, when passing through the inside of the probe 10, by the measured-gas G flowing in the measurement region R1. The component concentration of the measurement target component in the measured-gas G is calculated by measuring the absorption spectrum on the basis of the measurement signal acquired by the first optical receiver 22.

In the above-described probe-type gas analyzer 1, each of the optical emitter 21, the reflector 15, and the first optical receiver 22 need to satisfy predetermined conditions in a state of attachment at the installation site. The predetermined conditions include positional relationships between these optical components such that the emitted light L1 irradiated from the optical emitter 21 passes through the measurement region R1 and is reflected by the reflector 15, and the reflected light L2 passes back through the measurement region R1 and is incident on the first optical receiver 22.

In addition to the aforementioned optical system related to the measurement light passing through the measurement region R1, the gas analyzer 1 according to one or more embodiments includes another optical system that uses a portion of the measurement light irradiated by the optical emitter 21 as reference light. This optical system related to the reference light in the gas analyzer 1 is mainly described below.

The analysis unit 20 further includes a splitting unit 24, disposed between the optical emitter 21 and the measurement region R1, that splits off a portion of the measurement light irradiated from the optical emitter 21 to yield reference light. The splitting unit 24 includes any appropriate optical component that can split the measurement light into any proportions. For example, the splitting unit 24 includes a beam splitter.

The analysis unit 20 further includes a reference unit 25 that includes the same gas as the measurement target component in the measured-gas G. For example, the reference unit 25 includes a reference cell. The reference unit 25 includes a second optical receiver 26 for receiving the reference light that was split off by the splitting unit 24 and passed through the region including the gas. The second optical receiver 26 is, for example, disposed inside the reference cell constituting the reference unit 25. Like the optical emitter 21, the first optical receiver 22, and the calculation unit 23, the second optical receiver 26 is electrically connected to a plurality of electronic substrates.

The analysis unit 20 further includes a reflector 27 between the splitting unit 24 and the reference unit 25. The reflector 27 reflects the reference light, which was split by the splitting unit 24, towards the optical emitter 21. The reflector 27 includes any appropriate reflecting mechanism, such as a mirror, that acts on the reference light.

The analysis unit 20 further includes an optical component 28 between the splitting unit 24 and the reference unit 25. For example, the optical component 28 includes any appropriate optical lens that acts on the reference light. The optical lens is configured to condense the reference light. The optical component 28 includes a plano-convex lens, for example. The optical component 28 is fixed inside the analysis unit 20 so that the flat surface of the plano-convex lens faces the reference unit 25 and the convex surface of the plano-convex lens faces the opposite side from the reference unit 25.

The housing of the above-described analysis unit 20 has a module structure integrally storing the splitting unit 24, the reference unit 25, the second optical receiver 26, the reflector 27, and the optical component 28 in addition to the optical emitter 21, the first optical receiver 22, and the calculation unit 23. The optical emitter 21, the first optical receiver 22, and the reference unit 25 are arranged to be near each other in the up-down direction inside the analysis unit 20.

Figure 4:
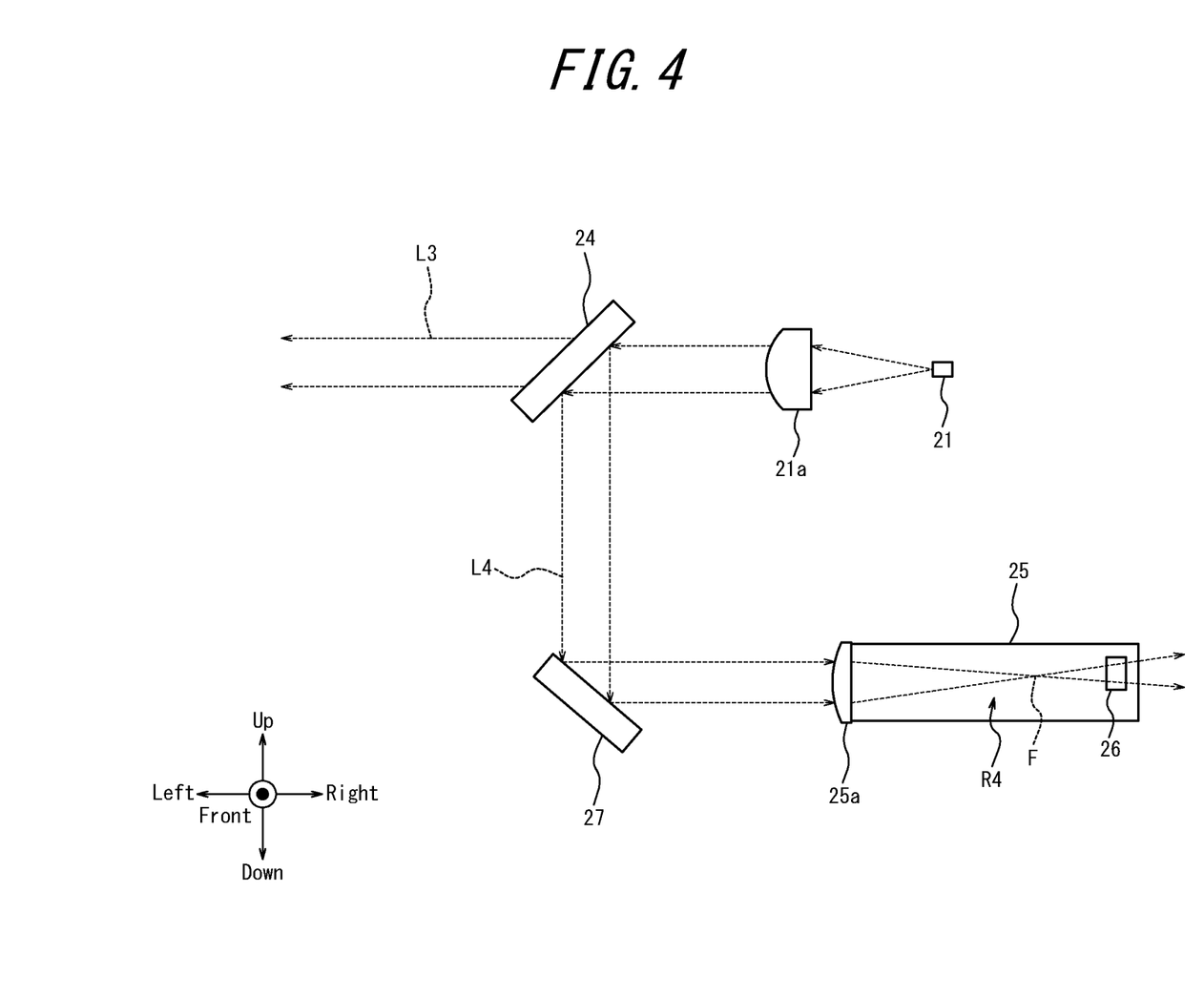
FIG. 4 schematically illustrates an optical system related to reference light when an optical component is not present in front of a reference unit inside an analysis unit, in accordance with one or more embodiments.

FIG. 4 schematically illustrates an optical system related to reference light L4 when the optical component 28 is not included in front of the reference unit 25 inside the analysis unit 20. FIG. 4 illustrates an example configuration of an optical system used in a known gas analyzer. After describing a portion of the functions of the optical system related to the reference light L4 with reference to FIG. 4, the problems occurring when the gas analyzer 1 does not include the optical component 28 are described.

The measurement light irradiated from the optical emitter 21 passes through an arbitrary optical lens 21a disposed on the exit face side of the optical emitter 21 and is split by the splitting unit 24 into measurement light L3 that propagates towards the measurement region R1 and reference light L4. The measurement light L3 that propagates towards the measurement region R1 corresponds to transmitted light in the splitting unit 24, for example. The reference light L4 corresponds to reflected light in the splitting unit 24, for example. The reference light L4 is reflected at a substantially right angle by the reflector 27 to be incident on the reference unit 25, which is arranged in parallel with the optical emitter 21. Specifically, the reference light L4 is incident on a condensing lens 25a attached to the entrance face of the reference unit 25. Subsequently, the reference light L4 is incident on the second optical receiver 26 of the reference unit 25.

A region R4 inside the reference cell constituting the reference unit 25 is filled with the same gas as the measurement target component, at a sufficiently known concentration for absorption spectrum measurement. The reference unit 25 uses the reference light L4 to output a TDLAS signal corresponding to the gas of known concentration. Accordingly, the absorption spectrum peak of the measurement target component is continually detected by the reference unit 25. For this reason, the reference unit 25 is often used when the concentration of the measurement target component in the measured-gas G is low. Since the absorbance of the measurement light L3 reduces in the case of low-concentration measurement, the peak intensity of the absorption spectrum of the measurement target component in the measured-gas G reduces. It is therefore difficult to detect the peak wavelength position accurately. Absorption spectrum measurement thus becomes difficult. To address such a problem, the reference unit 25 including the same gas as the measurement target component, at a sufficiently known concentration for absorption spectrum measurement, is provided. The wavelength position of the absorption spectrum peak of the measurement target component can be detected accurately with the reference unit 25 even during low-concentration measurement. Accordingly, the component concentration of the measurement target component in the measured-gas G can be analyzed accurately.

In the above-described gas analyzer 1, the optical emitter 21, the splitting unit 24, the reflector 27, the reference unit 25, and the second optical receiver 26 need to satisfy predetermined conditions. The predetermined conditions include positional relationships between these optical components such that the measurement light irradiated from the optical emitter 21 is incident on the splitting unit 24, the resulting reflected light is further reflected by the reflector 27 as the reference light L4, and the reference light L4 passes through the reference cell constituting the reference unit 25 and is incident on the second optical receiver 26.

Depending on the attachment requirements or attachment circumstances of the gas analyzer 1, however, the optical emitter 21, reflector 15, and first optical receiver 22 might not have appropriate positional relationships. For example, if the probe 10 that holds the reflector 15 at the tip of the probe 10 has a relatively narrow diameter (around 50 mm) and a length of approximately 0.5 m to 2 m, then the probe 10 warps under its own weight when attached in a cantilevered manner inside the flue P. This may cause the position and orientation of the reflector 15 to deviate from the design values. Furthermore, the housing of the analysis unit 20 that houses the optical emitter 21 and the first optical receiver 22 also warps under its own weight when attached in a cantilevered manner to the outside of the flue P. This may cause the position and orientation of the optical emitter 21 and the first optical receiver 22 to deviate from the design values. Consequently, the majority of the measurement light L3 is expected not to be incident on the reflector 15 in some cases. In these cases, the optical intensity of the measurement light L3 that returns to the first optical receiver 22 is greatly reduced. It therefore becomes difficult to acquire a scan signal with the intensity necessary for analysis, which reduces the measurement accuracy of the absorption spectrum.

To address this problem, the gas analyzer 1 may, for example, further include an appropriate alignment mechanism to adjust the beam position of the optical emitter 21, specifically the emission position of measurement light irradiated from the optical emitter 21. For example, the alignment mechanism includes any appropriate mechanism for adjusting the beam position of the optical emitter 21 from outside the analysis unit 20. The beam position of the optical emitter 21 in a direction substantially orthogonal to the optical axis of the measurement light is adjusted by such an alignment mechanism over a predetermined alignment range.

Here, the predetermined alignment range includes any range over which the beam position of the optical emitter 21 can be adjusted appropriately so that the measurement light L3 is reflected by the reflector 15 and returns to the first optical receiver 22. The predetermined alignment range may, for example, include an extra space, provided in the housing of the analysis unit 20, allowing alignment of the beam position of the optical emitter 21 in directions substantially orthogonal to the optical axis of the measurement light irradiated from the optical emitter 21. The predetermined alignment range may, for example, include a range of ±0.7 mm, in directions substantially orthogonal to the optical axis of the measurement light, from a standard position of the beam of the optical emitter 21.

The directions substantially orthogonal to the optical axis of the measurement light may, for example, include the up-down direction and front-back direction in FIG. 3, along with directions approximating these directions.

When the beam position of the optical emitter 21 is adjusted, however, the optical emitter 21, the reflector 27, and the second optical receiver 26 might not have appropriate positional relationships. For example, when the beam position of the optical emitter 21 approaches the upper limit position or the lower limit position of the predetermined alignment range, the reflection position of the reference light L4 in the splitting unit 24 shifts from when the beam position is at the standard position. Consequently, the optical intensity of the reference light L4 incident on the second optical receiver 26 of the reference unit 25 decreases. Specifically, when the beam position of the optical emitter 21 is at the standard position, the reference light L4 that passes through the condensing lens 25a of the reference unit 25 converges at a focal point F near the second optical receiver 26. The beam diameter of the reference light L4 incident on the second optical receiver 26 at this time is substantially equal to the receiving diameter of the second optical receiver 26. Accordingly, it is more difficult for the reference light L4 to be incident on the second optical receiver 26 when the beam position of the optical emitter 21 changes within the predetermined alignment range from the standard position. It therefore becomes difficult to acquire a sufficiently strong scan signal. In other words, it becomes difficult to detect the wavelength position of the absorption spectrum peak accurately even when using the reference unit 25.

In the gas analyzer 1 according to the present one or more embodiments, the optical component 28 is disposed in front of the condensing lens 25a of the reference unit 25, thereby allowing reference light L4 of sufficient optical intensity to be incident on the second optical receiver 26 even when the beam position of the optical emitter 21 changes from the standard position within the predetermined alignment range. Accordingly, the wavelength position of the absorption spectrum peak of the gas included in the reference unit 25 can be detected accurately.

Figure 5:
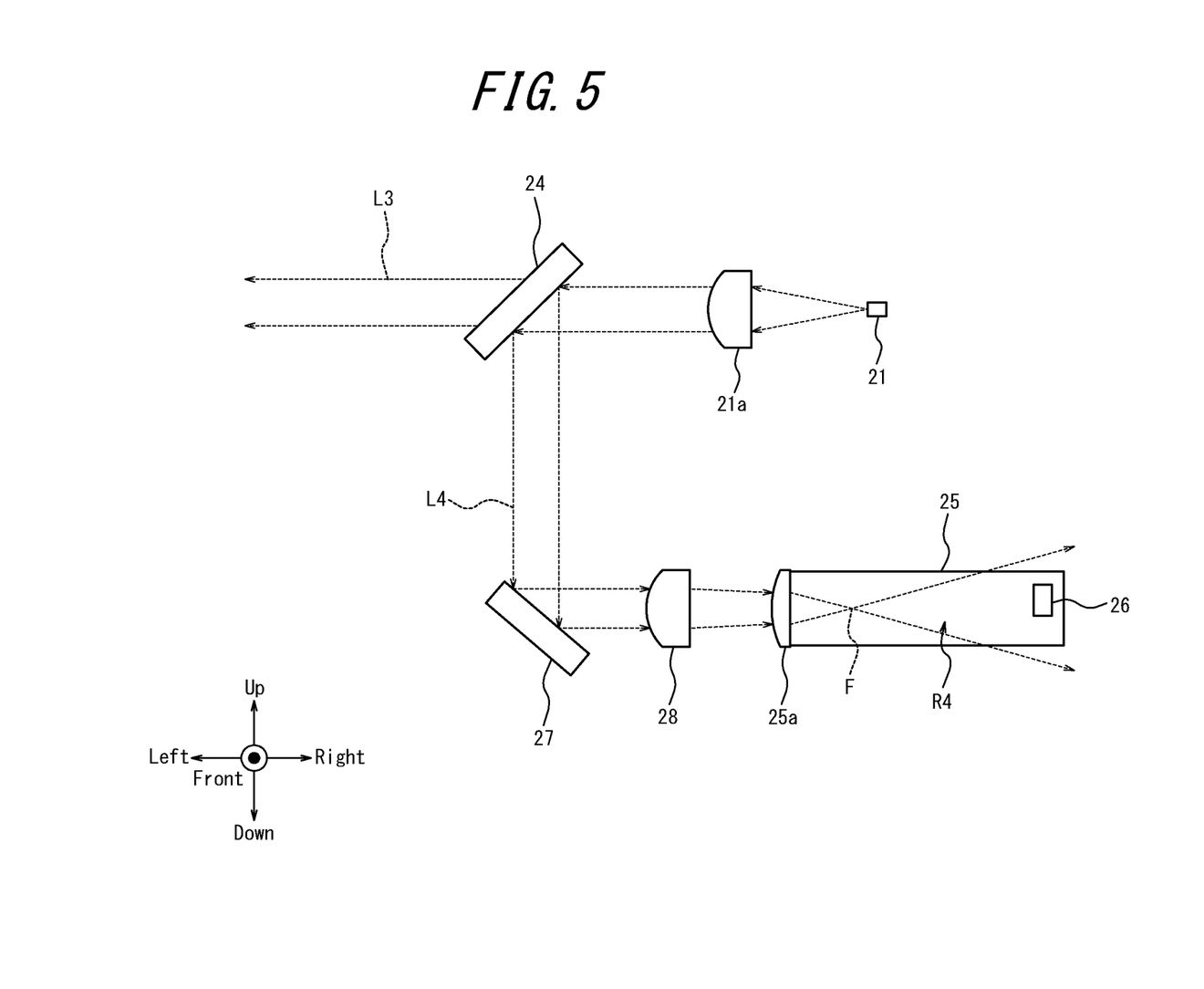
FIG. 5 is a schematic diagram that corresponds to FIG. 4 and illustrates an optical system related to reference light in the analysis unit of the gas analyzer in FIG. 1.
Figure 6:
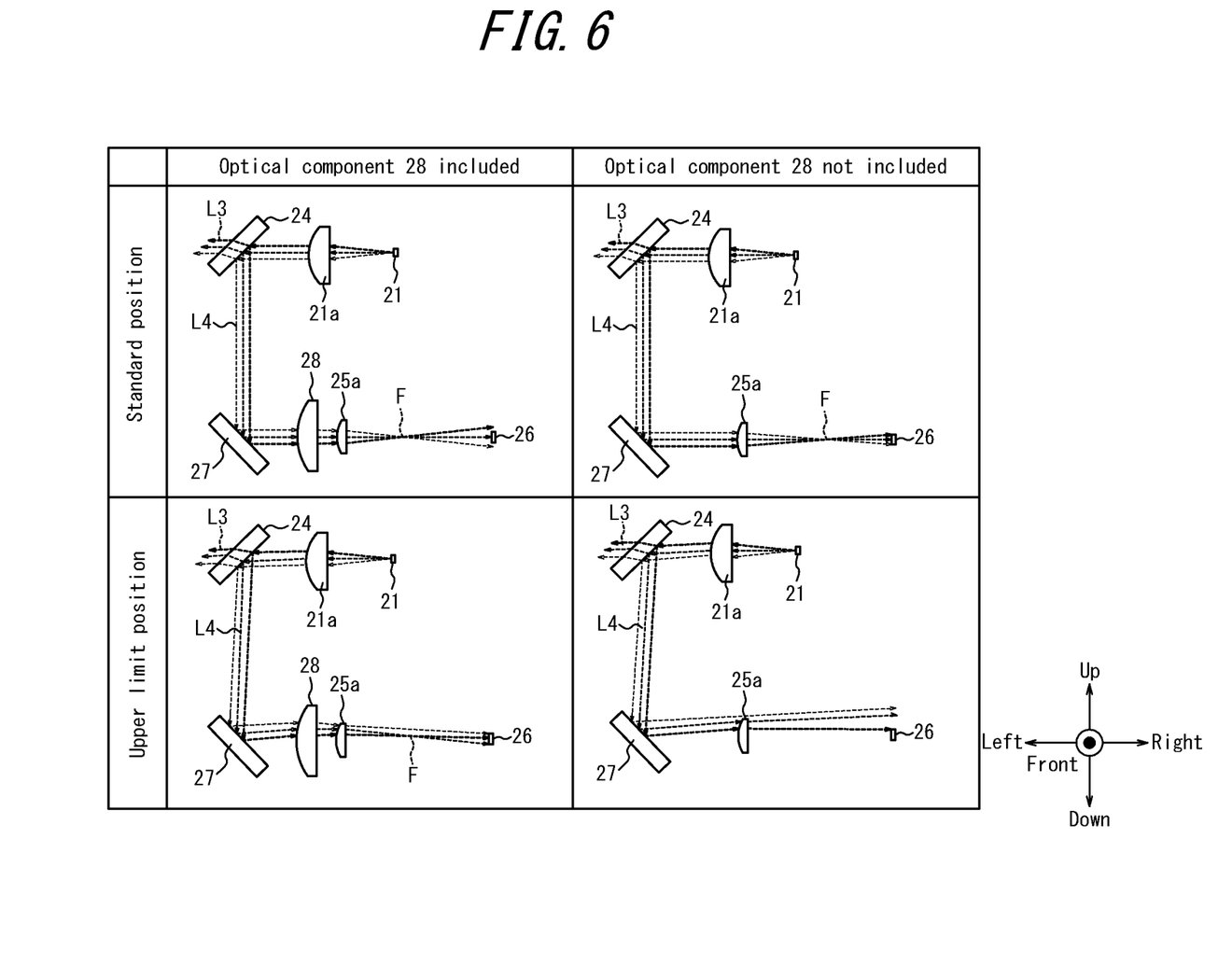
FIG. 6 is a schematic diagram comparing propagation of reference light in the analysis unit of the gas analyzer in FIG. 1 when an optical component is and is not included.

FIG. 5 is a schematic diagram that corresponds to FIG. 4 and illustrates the optical system related to the reference light L4 in the analysis unit 20 of the gas analyzer 1 in FIG. 1. FIG. 5 illustrates an example configuration of the optical system used in the gas analyzer 1 according to one or more embodiments of the present disclosure. FIG. 6 is a schematic diagram comparing propagation of the reference light L4 in the analysis unit 20 of the gas analyzer 1 in FIG. 1 when the optical component 28 is and is not included. The detailed structure and functions of the optical component 28 disposed inside the analysis unit 20 of the gas analyzer 1 according to one or more embodiments are described with reference to FIG. 5 and FIG. 6.

The optical component 28 adjusts the position of the focal point F of the reference light L4 in the reference unit 25 so that the reference light L4 is incident on the second optical receiver 26. The plano-convex lens constituting the optical component 28 is made of material corresponding to the wavelength characteristics of the reference light L4. For example, the plano-convex lens is made of material with good transmission characteristics with respect to the wavelength of the reference light L4. The plano-convex lens has a diameter such that the reference light L4 reflected by the reflector 27 can easily enter the plano-convex lens. For example, the plano-convex lens is formed to be as large as possible within the design tolerance of the analysis unit 20. The distance between the plano-convex lens and the reference unit 25 can be determined freely within the design tolerance of the analysis unit 20.

The plano-convex lens is configured to make a focal point F of the reference light L4 in the reference unit 25 closer to the plano-convex lens. Specifically, the plano-convex lens has a focal length that causes the focal point F of the reference light L4 in the reference unit 25 to be positioned closer to the plano-convex lens than when the gas analyzer 1 does not include the optical component 28. In other words, the plano-convex lens increases the beam diameter of the reference light L4 on the second optical receiver 26. The focal length of the plano-convex lens is set to a value that allows the second optical receiver 26 to receive the reference light L4 over the predetermined alignment range and that maximizes the irradiation intensity of the reference light L4.

If the beam position of the optical emitter 21 is at the standard position of the predetermined alignment range, then reference light L4 of sufficient optical intensity is incident on the second optical receiver 26 even when the gas analyzer 1 does not include the optical component 28, as illustrated in FIG. 6. At this time, the reference light L4 is focused once in the reference unit 25 by the condensing lens 25a of the reference unit 25 and then spreads again before being incident on the second optical receiver 26. The focal point F of the reference light L4 in the reference unit 25 is positioned closer to the second optical receiver 26 than when the optical component 28 is located in between. If the focal point F of the reference light L4 and the second optical receiver 26 are near each other, then the beam diameter of the reference light L4 at the second optical receiver 26 is small, and the optical intensity of the reference light L4 is high. Specifically, the beam diameter of the reference light L4 incident on the second optical receiver 26 is substantially equal to the receiving diameter of the second optical receiver 26.

However, when the beam position of the optical emitter 21 is at the upper limit position of the predetermined alignment range, for example, the reference light L4 does not focus after passing through the condensing lens 25a and is hardly incident on the second optical receiver 26.

On the other hand, when the gas analyzer 1 includes the optical component 28 and the beam position of the optical emitter 21 is at the standard position of the predetermined alignment range, then the optical component 28 causes the focal point F of the reference light L4 in the reference unit 25 to be positioned closer to the condensing lens 25a than when the gas analyzer 1 does not include the optical component 28. Consequently, the focal point F of the reference light L4 and the second optical receiver 26 are farther apart, but the beam diameter of the reference light L4 at the second optical receiver 26 is larger. The optical component 28 expands the beam diameter of the reference light L4 to be larger at the second optical receiver 26 than the receiving diameter of the second optical receiver 26. Specifically, the beam diameter of the reference light L4 at the second optical receiver 26 is several times larger than the receiving diameter of the second optical receiver 26. Accordingly, the reference light L4 reliably strikes the second optical receiver 26.

For example, even when the beam position of the optical emitter 21 is at the upper limit position of the predetermined alignment range, a portion of the reference light L4 is focused in the reference unit 25 by the optical component 28 and the condensing lens 25a. A portion of the focused reference light L4 spreads out again and reliably strikes the second optical receiver 26.

If the beam diameter of the reference light L4 at the second optical receiver 26 is expanded, the amount of the reference light L4 received by the second optical receiver 26 decreases. To increase the amount of the reference light L4 received by the second optical receiver 26, the gas analyzer 1 is normally configured for the beam diameter of the reference light L4 to be narrower than the receiving diameter of the second optical receiver 26, so that substantially all of the reference light L4 is incident on the second optical receiver 26. In one or more embodiments of the present disclosure, however, the beam diameter of the reference light L4 at the second optical receiver 26 is expanded to stabilize the amount of the reference light L4 received at the second optical receiver 26 even when the beam position of the optical emitter 21 changes from the standard position. The wavelength position of the absorption spectrum peak can be detected if a portion of the reference light L4 is incident with the minimum optical intensity necessary for absorption spectrum measurement.

As the optical intensity of the reference light L4 incident on the second optical receiver 26 is greater, the wavelength position of the absorption spectrum peak of the measurement target component can be identified more easily. A larger optical intensity is therefore normally preferred for the reference light L4 irradiated on the second optical receiver 26. If the position of the focal point F of the reference light L4 in the reference unit 25 is too close to the condensing lens 25a, however, the reference light L4 spreads out greatly after converging at the focal point F. The optical intensity of the reference light L4 irradiated onto the second optical receiver 26 then decreases. The position of the focal point F of the reference light L4 in the reference unit 25 is therefore determined by the tradeoff between the irradiation intensity of the reference light L4 at the second optical receiver 26 and the possibility of receipt by the second optical receiver 26 over the predetermined alignment range. For example, the position of the focal point F of the reference light L4 in the reference unit 25 is set to a value that allows the second optical receiver 26 to receive the reference light L4 over the predetermined alignment range and that maximizes the irradiation intensity of the reference light L4.

With the above-described gas analyzer 1 according to one or more embodiments, the amount of the reference light L4 received at the second optical receiver 26 is stable, even when the beam position of the optical emitter 21 changes from the standard position. Since the gas analyzer 1 includes the optical component 28, the reference light L4 reliably strikes the second optical receiver 26 even when, for example, the beam position of the optical emitter 21 is adjusted to either the upper limit position or the lower limit position of the predetermined alignment range. Accordingly, it is easy to detect the wavelength position of the absorption spectrum peak of the gas, which is identical to the measurement target component, filling the reference cell constituting the reference unit 25. In this way, measurement with the gas analyzer 1 that uses the reference unit 25 has better resistance to changes in the beam position of the optical emitter 21.

The analysis unit 20 overall becomes more compact by virtue of the reflector 27 being disposed in the analysis unit 20. In greater detail, electronic components and the above-described optical components need to be arranged together inside the analysis unit 20 in the probe-type gas analyzer 1. The interior space of the analysis unit 20 is efficiently used in this case as well, since the optical path of the reference light L4 turns back because of the reflector 27.

It will be clear to a person of ordinary skill in the art that the present disclosure may be implemented in certain ways other than the above embodiments without departing from the spirit or essential features thereof. Accordingly, the above explanation merely provides examples that are in no way limiting. The scope of the present disclosure is to be defined by the appended claims, not by the above explanation. Among all changes, various changes that are within the range of equivalents are considered to be included therein.

For example, the shape, arrangement, orientation, number, and the like of the above-described components are not limited to the above explanation or the drawings. The shape, arrangement, orientation, number, and the like of each component may be selected freely as long as the functions of the component can be achieved.

The optical component 28 has been described as including an optical lens, but this example is not limiting. The optical component 28 may include any part that can expand the beam diameter of the reference light L4 at the second optical receiver 26.

The optical component 28 has been described as causing the focal point F of the reference light L4 in the reference unit 25 to be positioned closer to the condensing lens 25a, but the alignment method is not limited to this example. The alignment method may include any method allowing the second optical receiver 26 to reliably receive the reference light L4 in the predetermined alignment range related to the beam position of the optical emitter 21. For example, the optical component 28 may position the focal point F on the opposite side of the second optical receiver 26 from the condensing lens 25a. In this case, the reference light L4 does not completely focus between the condensing lens 25a and the second optical receiver 26 but rather attempts to focus at the focal point F positioned behind the second optical receiver 26. Accordingly, the reference light L4 is incident on the second optical receiver 26 in a state with the beam diameter somewhat expanded.

The optical lens constituting the optical component 28 is not limited to being a plano-convex lens. The optical lens may include any lens allowing the second optical receiver 26 to reliably receive the reference light L4 in the predetermined alignment range related to the beam position of the optical emitter 21. For example, the optical lens may be a biconvex lens or a concave lens.

The gas analyzer 1 has been described as including an optical component 28 separate from the condensing lens 25a of the reference unit 25, but this example is not limiting. The optical component 28 may have any configuration in which the optical component 28 is arranged between the region R4 in which gas is included and the splitting unit 24 and that allows the second optical receiver 26 to reliably receive the reference light L4 in the predetermined alignment range. For example, a plano-convex lens constituting the optical component 28 may be attached at the position of the condensing lens 25a instead of the condensing lens 25a. The optical component 28 and the reference unit 25 may thus be formed integrally.

The second optical receiver 26 has been described as being disposed inside the reference cell constituting the reference unit 25, but this example is not limiting. The second optical receiver 26 may be disposed at any position allowing receipt of the reference light L4 that has passed through the gas filling the reference cell. For example, the second optical receiver 26 may be attached at the opposite end of the reference cell from the condensing lens 25a. The second optical receiver 26 may, for example, be disposed outside of the reference cell.

The gas analyzer 1 need not include the reflector 27 if space can be guaranteed in the analysis unit 20. At this time, the reference unit 25 is disposed along a straight optical path of the reference light L4 reflected by the splitting unit 24.

Both the emitted light L1 and the reflected light L2 have been described as passing through the measurement region R1, but this example is not limiting. Provided that the gas analyzer 1 is capable of analyzing the component concentration of the measurement target component in the measured-gas G included in the measurement region R1, it suffices if only one of the emitted light L1 and the reflected light L2 passes through the measurement region R1.

The gas analyzer 1 has been described as being a probe-type device but is not limited to this type. The gas analyzer 1 may, for example, be configured so that the optical emitter 21 and the first optical receiver 22 are separate bodies facing each other across the flue P. In this case, the gas analyzer 1 need not include the reflector 15, and the first optical receiver 22 may be positioned along the straight optical path of the measurement light L3 irradiated by the optical emitter 21. As a result, the number of parts in the components of the gas analyzer 1 arranged on both sides of the flue P is reduced, making the components more compact. The gas analyzer 1 may, for example, be configured so that the analysis unit 20 and the reflector 15 are separate bodies facing each other across the flue P. Specifically, any appropriate reflecting structure constituting the reflector 15 may be attached to the opposite side from the side of the flue wall S to which the analysis unit 20 is attached. In this case, the reflecting structure constituting the reflector 15 may, for example, be attached to the inner surface or the outer surface of the flue wall S.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

What is claimed is:

1. A gas analyzer comprising:
   an optical emitter that irradiates measurement light into a measurement region including a measured-gas;
   an alignment mechanism that adjusts an emission position of the measurement light irradiated from the optical emitter;
   a first optical receiver that receives the measurement light after the measurement light passes through the measurement region;
   a beam splitter disposed between the optical emitter and the measurement region and that splits off a portion of the measurement light irradiated from the optical emitter to yield reference light;
   a reference unit that comprises:
      a cell filled with gas at a known concentration, wherein the gas contains a component that is identical to a measurement target component in the measured-gas; and
      a second optical receiver that receives the reference light after the reference light passes through a region of the reference unit; and
   an optical component disposed between the beam splitter and the region of the reference unit,
   wherein the optical component expands a beam diameter of the reference light to be larger at the second optical receiver than a receiving diameter of the second optical receiver,
   wherein a focal length of the optical component is set to a value that:
      regardless of the emission position of the measurement light that is adjusted by the alignment mechanism, allows the second optical receiver to receive the reference light over an alignment range of the emission position in a direction orthogonal to an optical axis of the measurement light, and
      maximizes an irradiation intensity of the reference light onto the second optical receiver.

2. The gas analyzer of claim 1, wherein the optical component comprises an optical lens that condenses the reference light.

3. The gas analyzer of claim 2, wherein the optical lens places a focal point of the reference light in the reference unit closer to the optical lens than when the gas analyzer does not comprise the optical component.

4. The gas analyzer of claim 3,
   wherein the optical lens is a plano-convex lens; and
   wherein a flat surface of the plano-convex lens faces the reference unit.

5. The gas analyzer of claim 1, further comprising a first reflector disposed between the beam splitter and the optical component and that reflects the reference light split off by the beam splitter towards the optical component.

6. The gas analyzer of claim 5, further comprising:
   a probe extending along an optical axis of the measurement light such that the optical axis overlaps the measurement region; and
   a second reflector positioned at an opposite end of the probe from the optical emitter and that reflects the measurement light, wherein
   the first optical receiver receives the measurement light reflected by the second reflector.

* * * * *